US005119553A

United States Patent [19]

Sato

[11] Patent Number: 5,119,553

[45] Date of Patent: Jun. 9, 1992

[54] SPRING CLIP AND DRIVER THEREFOR

[76] Inventor: Hisao Sato, Fujimidai-Mansion 2002, 29-10, Nukui 1-Chome, Nerima-Ku, Tokyo, Japan

[21] Appl. No.: 546,442

[22] Filed: Jul. 2, 1990

[30] Foreign Application Priority Data

Jul. 2, 1989 [JP] Japan ............................ 1-78142[U]

[51] Int. Cl.[5] ............................................ A61B 17/00

[52] U.S. Cl. .................................. 29/243.56; 24/67.9

[58] Field of Search ....................... 24/563, 67.3, 67.5, 24/67.9, 561, 562; 29/243.56

[56] References Cited

U.S. PATENT DOCUMENTS

| | | | |
|---|---|---|---|
| 400,627 | 4/1889 | Angell | 24/563 |
| 1,236,654 | 8/1917 | Baltzley | 24/561 |
| 1,868,726 | 7/1932 | Collier | 24/561 |
| 3,294,229 | 12/1966 | McConnell et al. | 24/67.9 X |
| 3,797,076 | 3/1974 | Watkin | 24/67.9 X |
| 4,332,060 | 6/1982 | Sato . | |
| 4,353,157 | 10/1982 | Sato | 29/243.56 |
| 4,637,395 | 1/1987 | Caspar et al. | 29/243.56 X |
| 4,735,438 | 4/1988 | Demarest, Jr. | 24/67.5 X |
| 4,791,707 | 12/1988 | Tucker | 29/243.56 X |
| 4,854,317 | 8/1989 | Braun | 29/243.56 X |
| 4,996,755 | 3/1991 | Sato | 29/243.56 |

FOREIGN PATENT DOCUMENTS

| | | | |
|---|---|---|---|
| 1451469 | 9/1966 | France | 24/67.9 |
| 22195 | 11/1915 | United Kingdom | 24/563 |

*Primary Examiner*—James R. Brittain

*Attorney, Agent, or Firm*—Kanesaka and Takeuchi

[57] ABSTRACT

A spring clip for binding a material, such as papers, is formed of a pair of grasping portions and a connection portion for connecting the grasping portions. Each grasping portion has a trapezoid form surrounded by front and rear edges and two side edges. Also, each grasping portion has a flat outer surface, a flat inner surface and an inclined end surface at a free end or the front edge. When the grasping portions abut against each other, the inclined end surfaces form a gap therebetween. The clip is applied to the material by a clip driver formed of a casing for receiving the clip, and a knob for pushing the clip. A pair of clip opening spring members is attached to the casing for opening the clip when applying the clip to the material.

8 Claims, 4 Drawing Sheets

SPRING CLIP AND DRIVER THEREFOR

BACKGROUND OF THE INVENTION

1. Field of the Invention

The present invention generally relates to a clip for holding or binding documents, sheets of paper, or the like, and a driver for opening the clip so as to make the clip grasp documents or the like between grasping portions of the clip. The present invention particularly relates to a spring clip formed by an elastic single plate-like body which is bent to form a pair of grasping portions abutting against each other so that, in use, the grasping portions are opened in the directions opposite to each other so as to grasp documents or the like therebetween, and relates to a driver for driving such a spring clip to grasp documents or the like.

2. Description of the Prior Art

To bind a plurality of loose documents together, generally, a stapler, a Gem clip, or the like has been used. In a stapler, however, there has been a disadvantage in that the documents are injured because a staple accommodated in the stapler is stuck through the documents to bind them together. In the case of a Gem clip in which documents are inserted between double ring portions of the Gem clip so as to be bound together, on the other hand, there is a disadvantage in that the documents are apt to come off from the Gem clip and that the Gem clip is not suitable to clip a large number of documents together, although the Gem clip has an advantage in that the documents are not injured by the Gem clip. There has been therefore proposed a clip which is formed in such a manner that an elastic plate-like member is bent to form a pair of grasping portions abutting against each other at the extremities thereof and rotatable levers are provided outside the grasping portions so that the levers are operated by fingers to thereby open the nip between the grasping portions so as to grasp documents or the like therebetween. In the clip, however, there has been a disadvantage in that in order to bind a large number of documents together, the clip must be made large in size and the levers must be pushed with strong force to move the abutment surfaces away from each other. Such a clip is therefore unsuitable for a person whose finger force is weak. Further, the opposite side edges of the elastic plate member are arcuately outward curved so as to rotatably support the levers, and therefore if other documents are stacked on the documents bound together by this clip, there has been a possibility that the documents stacked on the documents bound together by such a clip may be injured by the curved portions of the clip.

In U.S. Pat. No. 4,332,060 patented Jun. 1, 1982, therefore, the invertor of this application has proposed a spring clip having no such levers as described above and also disclosed a driver for driving out such a spring clip. Referring to FIG. 1, the spring clip will be described. The spring clip 1 is made of an elastic plate-like metal sheet which has been bent at opposite ends of a connection portion 2 formed substantially at the central portion of the sheet so as to form a pair of grasping portions 3 with their free ends elastically abutting against each other. At the opposite edge sides of the free end of each grasping portion 3, lug portions 4 are integrally formed so as to project outward respectively. Thus, two pairs of vertically opposing lug portions 4 are formed at the free end and vertically opposite edge sides respectively so that each pair of lug portions 4 are vertically opposite to each other at each edge side at the free end of the clip 1. A slanting surface 5 is provided at the free end edge side of each grasping portion 3 including the pair of widthwise opposite lug portions 4 so that the respective slanting surfaces 5 of the pair of grasping portions 3 are made to slant in the direction to separate from each other. To bind documents or the like by use of the spring clip 1, a clip driver for opening the nip between the grasping portions 3 of the spring clip 1 is used. The clip driver has a clip accommodation portion for accommodating the spring clip 1 therein, a pair of clip opening portions fixed at the front end opposite sides of the accommodation portion respectively so that in use, the above-mentioned two pairs of lug portions 4 of the clip 1 are inserted into the clip opening portions so as to open the respective nips between the two pairs of lug portions 4 respectively, that is, open the nip between the grasping portions 3 against the elasticity of the clip 1, and a lever arranged to be slidably inserted into the accommodation portion from the rear end thereof so as to abut against the connection portion 2 of the clip 1 to thereby push the clip 1 to the clip opening portion so that the clip 1 is made to grasp documents or the like. Specifically, as shown in FIG. 2, each of the clip opening portions 6 of the clip driver is constituted by a base portion 7 and a pair of clip-opening spring portions 8. The base portion 7 has a thickness which can be inserted into the nip between the slanting surfaces 5. The pair of clip-opening spring portions 8 are extended from the front end of the base portion 7 and biased elastically in the direction so that the respective front ends of the clip-opening spring portions 8 separate from each other. The pair of clip opening portions 6 are arranged so that the nip between the slanting surfaces 5 at the above-mentioned two pairs of vertically opposite lug portions 4 of the clip 1 which are normally in contact with each other is inserted into the base portions 7. Accordingly, if the clip 1 is pressed by the lever toward the front end of the driver, into the base portions 7 the nip between the slanting surfaces 5 at the two pairs of vertically opposite lug portions 4 is inserted, and then the clip-opening spring portions 8 come into the respective nips between the two pairs of vertically opposite lug portions 4. The respective nips between the two pairs of vertically opposite lug portions 4 are opened by the spring force of the clip-opening spring portions 8 against the elasticity of the clip 1. Accordingly, a large gap is formed between the respective free ends of the grasping portions 3, and documents or the like are inserted into this gap. If the lever is further slid toward the front end of the driver in this state, the two pairs of lug portions 4 of the clip 1 are pushed out from the front ends of the clip-opening spring portions 8 respectively, so that the grasping portions 3 are urged to return to its initial state by the elasticity thereof to thereby grasp the documents therebetween.

Thus, in the conventional spring clip, the grasping portions 3 are opened by use of the lug portions 4 provided on the widthwise opposite side edges of the clip. Because the lug portions 4 are outward projected at the widthwise opposite side edges of the clip 1, however, there is a risk that documents may be often damaged by the corner portions of the lug portions 4 when the clip 1 is removed from the bound documents. On the other hand, the clip 1 is manufactured in such a manner that an elastic metal plate is first punched into a predetermined shape by means of a press and then the punchedout metal plate is subject to bending work in such a manner as described above. Accordingly, there is a possibility of occurrence of a burr on the periphery of the elastic metal plate in punch working. Such a burr not only may damage documents or the like but may injure a user per se. Accordingly, it is necessary to finish the clip 1 by grinding. It is however troublesome to finish the periphery of such small lug portions and the finishing work causes an increase in cost. There are further disadvantages in that the working with a metal mold is also troublesome because of existence of the lug portions 4 to thereby cause an increase in cost, and in that maintenance and check are also troublesome. Further, if the clip 1 is to be made of synthetic resin, the lug portions 4 must be reinforced with any material because stress is applied locally onto the lug portions 4 in opening the clip 1. Accordingly, it has been necessary to mainly use a metal plate to produce the clip 1.

SUMMARY OF THE INVENTION

It is therefore an object of the present invention to provide a spring clip which has a simple shape, which can be inexpensively manufactured, and which never damage documents or the like when the clip is removed from the documents or the like.

It is another object of the present invention to provide a spring clip which can firmly bind documents or the like not only when the clip is made of an elastic thin metal plate but even when it is made of a synthetic resin material.

It is a further object of the present invention to provide a clip driver for binding documents or the like by using such a spring clip as described above.

It is a still further object of the present invention to provide a clip driver which can be assembled easily with a reduced number of parts.

In order to attain the above objects, according to an aspect of the present, provided is a spring clip made of a single elastic belt-like plate member, the spring clip comprising a connection portion provided substantially at a longitudinal center of the belt-like elastic plate member and a pair of grasping portions having one ends integrally continued to the connection portion and the other ends which are free ends elastically contacting with each other, the free ends being opened against the elasticity of the connecting portion when a force is exerted to a nip between the free ends of the respective grasping portions so that plural sheets of paper or the like can be inserted between the free ends so as to be elastically grasped therebetween when the force is removed, each of the grasping portions being defined by a front edge forming the free end, a rear edge forming a boundary between the grasping portion and the connection portion, and widthwise opposite side edges each connecting the front edge and the rear edge at widthwise opposite sides of the grasping portion, each of the grasping portions having a width which is wider at the front edge than at the rear edge, each of the widthwise opposite side edges extending substantially linearly, the grasping portions having end surfaces at the free ends respectively, the end surfaces being formed so as to have a gap therebetween at the front edges of said respective grasping portions.

According to another aspect of the present invention, provided is a clip driver for binding documents or the like by using the above clip according to the first aspect of the invention, the clip driver comprising: a lower casing having at its front end a lower opening portion forming a part of an insertion inlet for the documents or the like, the lower casing having an upper surface on which at least one the clip is mounted with the grasping portions made directed toward the insertion inlet so that the clip is slidable in a longitudinal direction of the clip driver; an upper casing having at its front end an upper opening portion forming the insertion inlet together with the lower opening portion of the lower casing and having at its rear end a clip insertion inlet for inserting the clip; a knob mounted in a rectangular opening which is formed in the upper casing at its front end side so as to extend in the longitudinal direction, the knob being slidable in the longitudinal direction and being movable up and down within a predetermined range, the knob having a knob projection portion projected upward from the opening, a push-out portion formed on a front end of the knob projection portion so that the push-out portion comes to abut on the bent portion of the clip when the knob is lowered, and a projection portion rearward extending from a rear end of the knob projection portion; a pair of clip opening spring members provided in the insertion inlet formed by the lower and upper casings for opening the grasping portions of the clip in the directions opposite to each other, each of the clip opening spring members having a base portion having a thickness capable of being inserted into the gap of the clip, and a pair of spring leg portions extending from a front end of the base portion and elastically biased in the direction so as to separate from each other, the clip opening spring members being disposed in the casing so that the distance between opposite inner side edges of the two base portions is made longer than the width of each of the grasping portions at the rear edge thereof of the clip while shorter than the width of each of the grasping portions at the front edge thereof, the pair of spring leg portions being tapered at front end side edges opposite to each other of the respective spring leg portions so that the interval between the front end opposite sides edges of the respective spring leg portions becomes wider than the width of the front edges of the clip as the front edges of the clip approach the front ends of the spring leg portions.

According to the present invention, having no lug portions which have been necessarily provided in the conventional spring clip as described above, the spring clip never damages documents when the clip is removed from the documents or when other documents are put on the documents bound by the clip. Further, since the front edges of the grasping portions are opened by inserting the clip-opening spring members into the widthwise opposite end corner portions at the front edge of the clip, the stress applied onto the spring clip in opening the clip is received on wider areas in comparison with the conventional lug portion. Accordingly, the required strength is enough to be smaller than that of the conventional clip, so that the clip can be made of synthetic resin through molding and various colored spring clips can be therefore provided at a low cost.

These and other object and advantages of the present invention will become apparent from the following description about the preferred embodiments of the present invention.

DETAILED DESCRIPTION OF THE PREFERRED EMBODIMENTS

Preferred embodiments of the spring clip and the clip driver according to the present invention will be described with reference to the accompanying drawings hereunder. In the following description, the terms "front" and "rear" are defined to be the respective sides from which a spring clip (hereinafter simply referred to "a clip") is driven out of and inserted into a clip driver, respectively. Further, the same constituent members in the embodiments are correspondingly referenced and the description thereof will be omitted.

Figure 1:
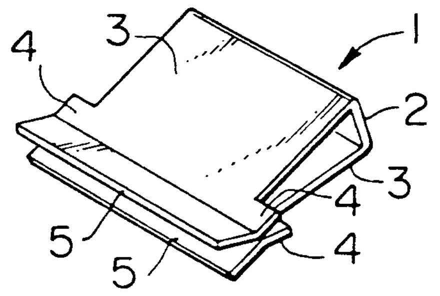
FIG. 1 PRIOR ART
FIG. 1 is a perspective view showing an example of a conventional spring clip.
Figure 2:
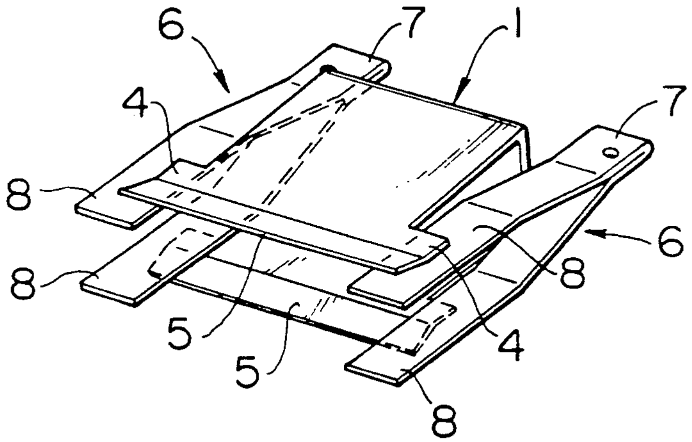
FIG. 2 PRIOR ART
FIG. 2 is a perspective view for explaining the relation between the clip and clip-opening portions provided in a clip driver so as to open the spring clip of FIG. 1.
Figure 3:
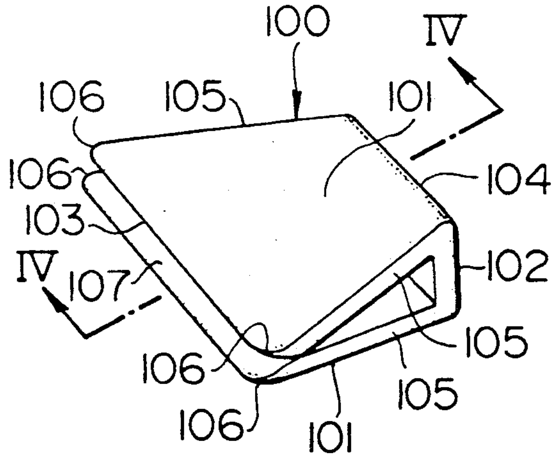
FIG. 3 is a perspective view showing an embodiment of the spring clip according to the present invention.
Figure 4:
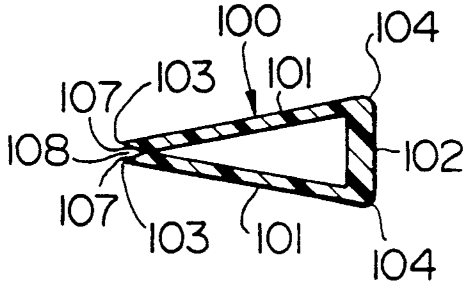
FIG. 4 is a vertical section view of the spring clip of FIG. 3 along IV—IV line.

First, referring to FIGS. 3 and 4, a first embodiment of the clip will be described. A clip 100 is made of a single elastic plate-like member of synthetic resin and is constituted by a pair of flat grasping portions 101 and a connection portion 102 by which the grasping portions 101 are connected to each other at the respective rear ends thereof. Each of the grasping portions 101 has a substantially trapezoidal form defined by a front edge 103, a rear edge 104 shorter in width than the front edge 103, and widthwise opposite side edges 105 each extending so as to connect the front edge 103 and the rear edge 104. Widthwise opposite corner portions 106 at junctions between the front edge 103 and the widthwise opposite side edges 105 are made round properly. As shown in detail in FIG. 4, slanting end surfaces 107 are formed at the front edges 103 of the grasping portions 101 respectively in a manner so that a gap 108 formed between the slanting end surfaces 107 becomes wider gradually toward the front edges 103. The grasping portions 101 are bent at the respective rear edges 104 thereof, that is, at the upper and lower ends of the connection portion 102, so that the respective slanting surfaces 107 of the front edges 103 come into elastic contact with each other at the rear ends thereof. The connection portion 102 has a certain height equal to a thickness of plural sheets of paper to be bound together.

Referring to FIGS. 5 through 9, the clip driver for driving the clip 100 to bind documents or the like will be described hereunder. The clip driver 11 is constituted mainly by a rectangular lower casing 12, and an upper casing 13 attached on the lower casing 12 so as to cover the lower casing 12, and a knob 14 attached on the upper casing 13 slidably in the longitudinal direction of the upper casing 13. All the lower casing 12, the upper casing 13, and the knob 14 are formed of synthetic resin. A lower inclination rim 15 is formed on the periphery of a front end portion of the lower casing 12 so as to be upward obliquely inclined toward a rear end portion of the lower casing 12, and, on the other hand, an upper inclination rim 16 is formed on the periphery of a front end portion of the upper casing 13 so as to be inclined downward obliquely toward a rear end portion of the upper casing 13. When the lower and upper casings 12 and 13 have been assembled, the lower and upper inclination rims 15 and 16 form an insertion inlet 17 at the front end of the assembly of the lower and upper casings 12 and 13 so that documents or the like to be bound together are inserted thereinto.

In the lower casing 12 of the clip driver 11, clip opening spring members 21, which will be described later in detail, are attached to the lower casing 12 at the widthwise opposite sides of the longitudinal front end portion thereof where the insertion inlet 17 is formed. Each of the clip opening spring members 21 has a substantially lateral-turned V-shape in cross section and has an insertion hole 22 formed in the vicinity of the vertex of the V-shape thereof. The clip opening spring members 21 are pressed so that the insertion holes 22 thereof are fitted onto corresponding upstanding pins 23 formed on the lower casing 12 integrally therewith so that the clip opening spring members 21 are attached to the lower casing 12. The positions of the insertion holes 22 and pins 23 are selected so that the respective inner side edges of the clip opening spring members 21 never come into contact with the connection portion 102 of the clip 100 while the pairs of the upper and lower corner portions 106 of the clip 100 are inserted into the clip opening spring member 21. The lower casing 12 has a longitudinally extending groove 24 formed therein. The width of the groove 24 is selected so as to be substantially equal to the width of the front edges 103 of the respective grasping portions 101 of the clip 100 so that the clip 100 can be inserted into the groove 24. A recess 25 lowered in level than the groove 24 is formed in a front end portion of the groove 24 in the lower casing 12. A front end groove 26 which is deeper than the groove 24 but shallower than the recess 25 is formed also in the lower casing 12 so as to extend from the substantially central portion of the recess 25 toward the front end of the casing 12. A pair of guide step portions 28 for holding thereon the widthwise opposite side end portions of the front edges 103 of the clip 100 are formed on widthwise opposite side walls 27 of the groove 24 at the inside lower portions thereof so as to longitudinally extend to the vicinity of the vertexes of the clip opening spring members 21 respectively. Further, the lower casing 12 is provided, at its rear end portion, with a pair of guide projections 29 inclined downward from the rear end portion of the lower casing 12 toward the front end of the same so as to be continued to the guide step portions 28 respectively. The rear end portions of the respective guide projections 29 are connected to each other through a horizontally extending connection portion 31. A pair of fitting rims 32 are formed on the respective upper surfaces of the pair of side walls 27 so as to make the lower casing 12 fit into the upper casing 13, and a pair of upstanding pins 33 are formed in the vicinity of the pins 23 so as to fit into fitting holes (not shown) formed in the upper casing 13. The front end portions of the guide step portions 28 positioned under the clip opening spring members 21 have engagement step portions 34 having upper surface portions lower than the guide step portions 28 respectively. The opposite side edges of the respective clip opening spring members 21 are partly disposed on the engagement step portions 34. A widthwise elongated groove 35 is formed in the outer periphery of the lower casing 12 at a portion corresponding to the clip opening spring members 21. A recess portion 36 is formed in the outside lower surface of the bottom of the lower casing 12 at a portion between the groove 35 and the position corresponding to the recess 25 so that an operator may put his/her forefinger in the recess portion 36 when using the clip driver 11. A pair of spring sockets 37 are formed in the lower casing 12 at the front end opposite side portions thereof surrounded by the lower inclination rim 15 so that the front ends of the one leg portions of the clip opening spring members 21 are removably accommodated in the spring sockets 37 respectively.

Figure 5:
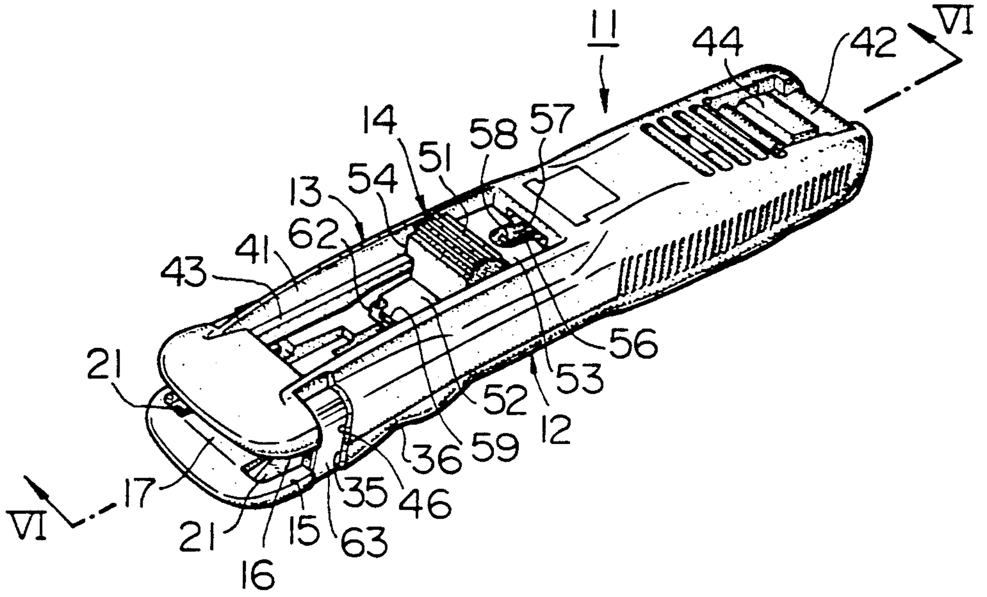
FIG. 5 is a perspective view showing an embodiment of the clip driver for opening the clip.
Figure 6:
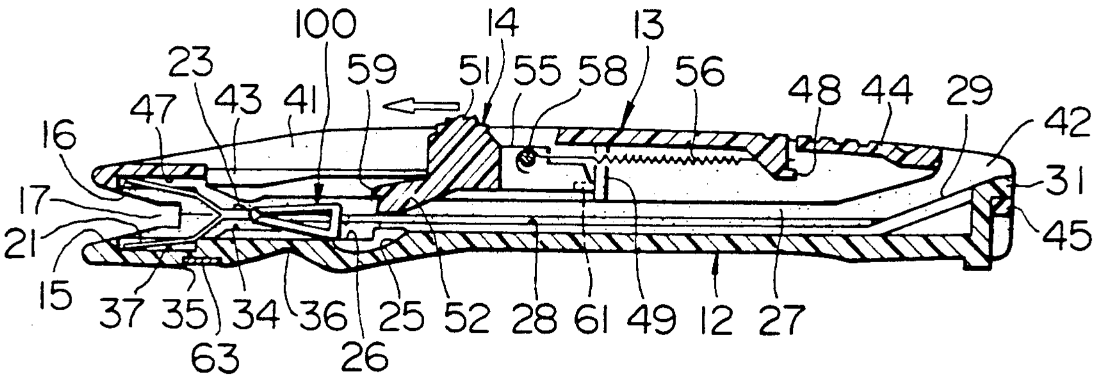
FIG. 6 is a vertical section view of the clip driver of FIG. 5 along VI—VI line under the condition that the knob has been displaced to the front end.
Figure 7:
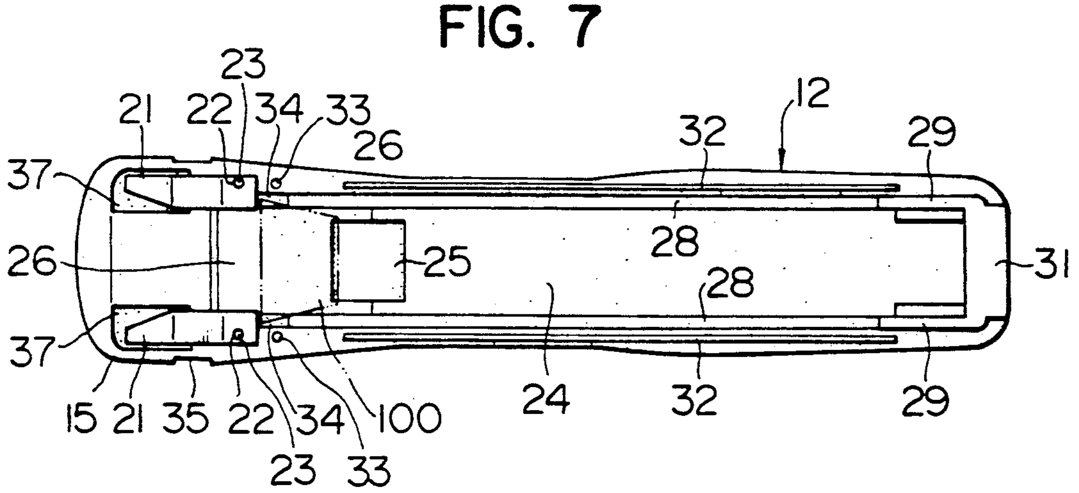
FIG. 7 is a plan view showing only the lower casing of FIG. 5.

The upper casing 13 generally having an inverted elongated dish shape is provided with a rectangular opening 41 formed therethrough so as to extend from the substantially longitudinally central portion toward the front end thereof and a clip insertion inlet 42 formed at the rear end thereof as shown in FIGS. 5 and 6. A pair of horizontally extending guide rims 43 is formed on the widthwise opposite inner side surfaces of the opening 41. A cover portion 44 for preventing an inserted clip 100 from coming off is formed at the clip insertion inlet 42 so as to extend from the front end of the clip insertion inlet toward the rear end of the same. The cover portion 44 is made to have elasticity so that the cover portion may be elastically vertically biased. The gap between the rear or free end of the cover portion 44 and the connection portion 31 of the lower casing 12 is selected so as to be a little narrower than the height of the connection portion 102 of the clip 100. A step portion 45 is formed on the rear end portion of the upper casing 13 so that the step portion 45 may abut on the lower surface of the connection portion 31 of the lower casing 12. Grooves 46 are formed in the front end portion of the upper casing 13 at its widthwise opposite sides so that the grooves 46 communicate with the groove 35 when the upper casing 13 is fitted into the lower casing 12. The respective front ends of the guide rims 43 extend to the vicinity of the respective vertexes of the clip opening spring members 21, and spring sockets 47 for removably accommodating the respective other leg portion front ends of the clip opening spring members 21 are formed at portions between the front ends of the guide rims 43 and the upper inclination rims 16.

The knob 14 is slidably inserted into the opening 41 of the upper casing 13 as shown in FIGS. 5 and 6. The knob 14 is constituted by integrally formed three portions, that is, a knob projection portion 51 with its top end projected upward from the opening 41, a push-out portion 52 frontward-downward projected from the knob projection portion 51 for abutting, at its front end, against the connection portion 102 of the clip 100 disposed at the head of the inserted clips, and a horizontal portion 53 substantially horizontally rearward extending from the rear end of the knob projection portion 51. The respective lower portions of the knob projection portion 51 and horizontal portion 53 and the push-out portion 52 are positioned between the guide rims 43. Opposite side portions 54 of the knob projection portion 51 extend so that the lower end surfaces of the opposite side portions 54 are respectively located above the upper surfaces of the respective guide rims 43 with a predetermined gap therebetween. The horizontal portion 53 is provided, at its knob projection portion 51 side, with extending portions 55 so that the lower end surfaces of the extending portions 55 are respectively located above the upper surfaces of the guide rims 43 with a predetermined gap therebetween. A spring 56 is stretched between the rear end of the upper casing 13 and the horizontal portion 53 so that the knob 14 is always pulled elastically rearward by the spring 56. Specifically, a notched portion 57 extending in the sliding direction of the knob 14 is formed substantially at the widthwise central portion in the rear portion of the horizontal portion 53 so that the opened end of the notched portion 57 is located at the rear end portion of the horizontal portion 53 and an engagement member 58 is formed in the notched portion 57. An engagement projection 48 is formed on the lower surface of the rear end portion of the upper casing 13 so as to project rearward, the spring 56 being hung, at its opposite ends, to the engagement member 58 and the engagement projection 48 respectively. An engagement portion 59 is formed integrally with the push-out portion 52 on the front end upper surface thereof so as to project a little from the front edge of the push-out portion 52 so that the engagement portion may engage with the upper shoulder portion of the connection portion 102 of the clip 100.

The horizontal portion 53 of the knob 14 has a pair of rear horizontal projections 61 formed at rear opposite sides thereof so as to horizontally sideward extend toward the opposite side surfaces of the opening 41 to thereby engage with the lower surfaces of the guide rims 43 respectively. On the other hand, the push-out portion 52 has front horizontal projections 62 formed at the front end upper surface thereof so as to extend horizontally sideward so that the front horizontal projections 62 engage with the lower surfaces of the guide rims 43 respectively. Thus, the knob 14 is disposed so as to sandwich the guide rims 43 between the respective lower surfaces of the side portions 54 of the knob projection portion 51 and the respective upper surfaces of the rear and front horizontal projections 61 and 62 so that the knob 14 may be slidably moved without coming off from the opening 41.

The rearward displacement of the knob 14 by the spring 56 is limited by abutment of the rear edge of the horizontal portion 53 against a limit projection 49 integrally formed on the rear side lower surface of the upper casing 13. The rear edge portion of the horizontal portion 53 which may abut against the limit projection 49 is lower than the engagement projection 48 and tapered so that the lower edge of the rear edge portion is more projected rearward than the upper edge of the same. Thus, although elastic force is applied onto the knob 14 by the spring 56 so as to rotate the knob 14 clockwise about the rear edge of the horizontal portion 53 in FIG. 6, the rotation force of the knob 14 is limited because the front horizontal projections 62 of the push-out portion 52 engage with the lower surfaces of the guide rims 43 respectively, so that the knob 14 is substantially horizontally elastically supported. The length of the front end portion of the push-out portion 52 is selected so that the front end portion of the push-out portion 52 is positioned substantially at the rear end portion of the recess 25 when the rear edge of the horizontal portion 53 engages with the limit projection 49.

The lower and upper casings 12 and 13 are fixed to each other by fitting a fastening band 63 formed of springy metal and having a substantial C shape into the grooves 35 and 46 formed in the outer peripheries of the lower and upper casings 12 and 13 respectively.

Figure 8:
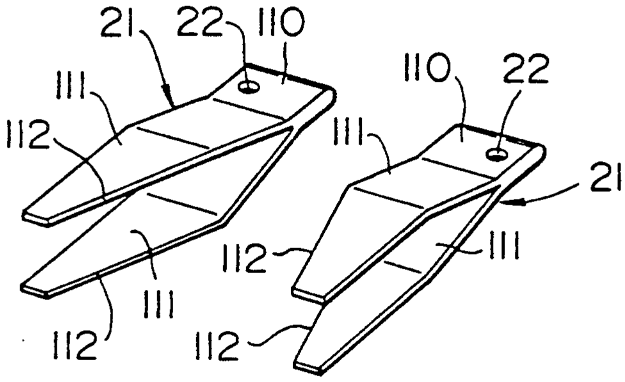
FIG. 8 is a perspective view showing only the clip-opening portions of FIG. 5.

As shown in detail in FIG. 8, each of the clip opening spring members 21 is constituted by a base portion 110 having a thickness smaller than the gap between the front edges 103 of the clip 100, and a pair of spring leg portions 111 extending from the front end of the base portion 110 and elastically biased in the direction so as to separate from each other. The above-mentioned insertion hole 22 is formed at near the rear end portion of each base portion 110. The pair of clip opening spring members 21 is attached in the lower casing 12 in a manner so that the distance between the opposite inner side edges of the base portions 110 of the respective clip opening spring members 21 is longer than the width of the connection portion 102 while shorter than the width of the front edge 103 of the clip 100. The inner side edge of the spring leg portion 111 of each of the pair of clip opening spring members 21 extends from the base portion 110 to extend substantially the longitudinally center portion thereof along the straight line of extension of the inner side edge of the base portion 110 and further extends from the center portion to the front end thereof so as to slant to form a slanting side edge 112. The widthwise opposite slanting side edges 112 of the respective spring leg portions 111 of the pair of clip opening spring members 21 are established so that the distance between those widthwise opposite side edges 112 is longer than the width of the front edge 103 of the clip 100 in the range from substantially the longitudinally center of each of the side edges 112 to the front edge of the same.

Assembling of the clip drier 11 will be described. First, the knob 14 is fitted into the opening 41 of the upper casing 13. This operation of insertion is performed as follows. The knob 14 is oriented substantially at right angles relative to the longitudinal direction of the opening 41 and then the front end of the push-out portion 52 is inserted into the opening 41 at the front end thereof. Then, the knob 14 is turned so that the horizontal portion 53 is located above the opening 41 while making the front horizontal projections 62 of the push-out portion 52 positioned under the lower surfaces of the guide rims 43 respectively. As a result, the front horizontal projections 62 of the push-out portion 52 are located under the lower surfaces of the guide rims 43 respectively, and the rear horizontal projections 61 of the horizontal portion 53 are located on the upper surfaces of the guide rims 43 respectively. Since the rear horizontal projections 61 are formed on the rear end side surfaces of the notched portion 57, the opposite-side portions of the notched portion 57 are made elastic. Accordingly, if these opposite-side portions are pushed toward the notched portion 57, the horizontal portion 53 can be easily inserted into the opening 41. Next, one and the other ends of the spring 56 are hung to the engagement member 58 and the engagement projection 48 respectively.

The clip opening spring members 21 are attached onto the lower casing 12 by fitting the insertion holes 22 onto the two pins 23 so that the respective openings of the clip opening spring members 21 are directed to the front end of the lower casing 12 and that the clip opening spring members 21 are in parallel to each other. Next, the lower casing 12 is covered with the upper casing 13 while making the rear end portion 45 of the upper casing 13 abut on the lower surface of the connection portion 31 of the lower casing 12. If grooves are formed in the lower end opposite side surfaces of the upper casing 13 so that the fitting rims 32 of the lower casing 12 may be fitted into the grooves, the casings 12 and 13 can be assembled without slipping. Further, the pins 23 and 33 are fitted into holes which are formed in the upper casing 13. As a result, a path for the clip 100 is formed in the inside of the lower and upper casings 12 and 13. Finally, the fastening band 63 is fitted into the grooves 35 and 46 to thereby complete the assembling of the clip driver 11. Although the two pins 23 and 33 are provided in this embodiment, only one pin 23 may be sufficient.

Thus, the clip driver 11 is constituted by six kinds of seven parts, that is, the lower casing 12, the upper casing 13, the knob 14, the pair of metal clip opening spring members 21, the spring 56, and the fastening band 63. It is therefore possible to reduce the parts in number in comparison with the conventional clip driver. Each of the lower casing 12, the upper casing 13, and the knob 14 can be integrally formed and therefore can be easily produced through injection molding or the like. Further, such assembling as described above can be extremely easily performed without using any special tool.

When documents are to be bound together by the clip 100, the clip 100 is inserted from the clip insertion inlet 42 with the front edges 103 of the clip 100 oriented frontward. Although the longitudinal size of the clip insertion inlet 42 is narrower than the height of the connection portion 102 of the clip 100 because of provision of the cover portion 44, the cover portion 44 can be lifted by insertion of the clip 100 so that the clip 100 can be inserted with small force. The opposite side corner portions 106 of the clip 100 are mounted on the guide step portions 28 of the lower casing 12 respectively and the connection portion 102 of the clip 100 rests on the bottom portion of the groove 24. If the clip driver 11 is inclined with the insertion inlet 17 made lower after one or more clips 1 have been accommodated in the groove 24 in a manner as described above, the connection portion 102 of the head clip 100 at the head of the clips is inserted into the front end groove 26, and at the same time, the widthwise opposite side corner portions 106 of the same clip 100 are positioned on the engagement step portions 34 respectively. Thus, the clip 100 at the head is in a lowered position. The location of the clip 100 in such a lowered position is to bring the gap 108 between the front edges 103 of the clip 100 to the base portions 110 of the respective clip opening spring members 21. In this location, the base portions 110 of the respective clip opening spring members 21 are located in the gap 108 between the front edges 103 so as to come into contact with the abutting portion between the two grasping portions 101. The height of the engagement step portions 34 is therefore adjusted in advance so that the base portions 110 of the respective clip opening spring members 21 are even in level to the gap 108 between the front edges 103 of the clip 100.

Figure 9:
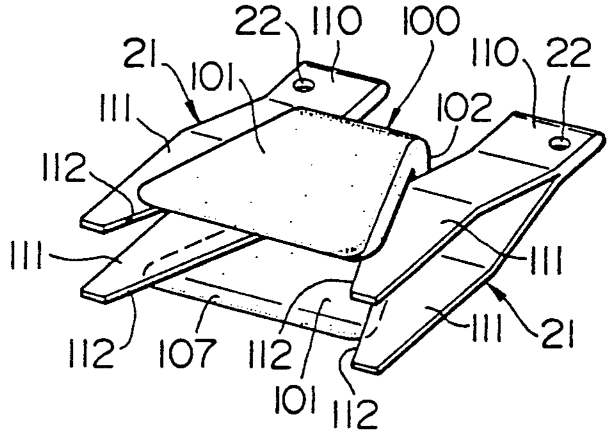
FIG. 9 is a perspective view for explaining the relation between the clip and the clip-opening portions.
Figure 10:
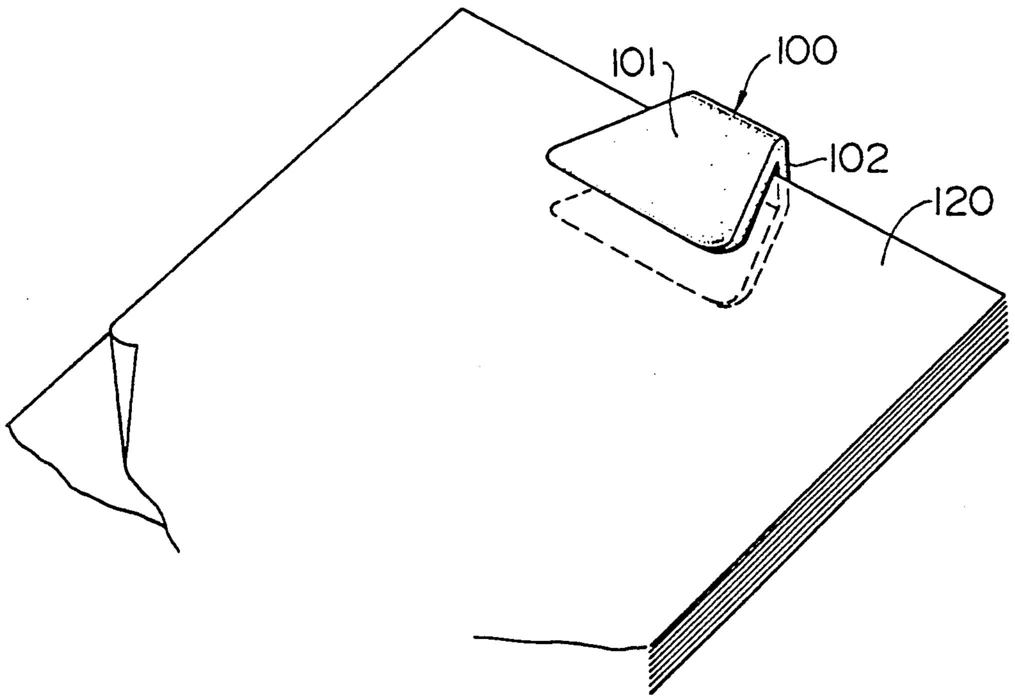
FIG. 10 is a perspective view showing the state in which documents are bound by the clip.

Then, the clip driver 11 is held by one hand with a forefinger put in the recess portion 36 and with a thumb put on the knob projection portion 51 of the knob 14, and then the knob projection portion 51 is pushed down by the thumb. As a result, the front end push-out portion 52 and the knob projection portion 51 of the knob 14 supported substantially horizontally by the spring 56 are lowered so that the lower end surfaces of the opposite side portions 54 of the knob projection portion 51 abut on the upper surfaces of the guide rims 43. With this state kept, the knob 14 is slid toward the insertion inlet 17. As a result, the front end of the push-out portion 52 abuts on the connection portion 102 of the head clip 100. Then, if the knob 14 is slid frontward against the spring force of the spring 56, the clip 100 is advanced by the knob 14 to enter into the gap 108 between the base portions 110 of the respective clip opening spring members 21, that is, between the two pairs of vertically opposing corner portions 106 of the clip 100. If the knob 14 is further slid frontward, the spring leg portions 111 of the respective clip opening spring members 21 come into the gap between the two pairs of vertically opposing corner portions 106 of the clip 100 so that the grasping portions 101 of the clip 100 are urged to open against the spring force thereof by the elasticity of the spring leg portions 111. When the front edges 103 of the clip 100 are located at the insertion inlet 17, the pair of grasping portions 3 are opened substantially parallel to each other, as shown in FIG. 9, so that the documents or the like can be inserted into the gap therebetween. If the knob 14 is further advanced, the opposite side corner portions 106 of the clip 100 are located at the front ends of the slanting side edges 112 of the respective spring leg portions 111. Since the distance between the widthwise opposite slanting side edges 112 at the front ends thereof is established to be longer than the width of the front edges 103 of the clip 100, the engagement between the widthwise opposite side corner portions 106 and the slanting side edges 112 of the respective spring leg portions 111 is released so that the clip 100 can be ejected from the insertion inlet 17. Thus, the clip 100 grasps documents or the like in the gap between the grasping portions 101 as shown in FIG. 10. The maximum thickness of documents which can be bound together is substantially equal to the height of the connection portion 102 of the clip 100.

When the next clip 100 is disposed at the head position, the knob 14 is released from the finger and the clip driver 11 is inclined so as to make the insertion inlet 17 on the front end of the clip driver 11 a little lower than the horizontal level so that the next clip comes into the recess 25. That is, the push-out portion 52 of the knob 14 is returned to the upper original position by the function of the spring 56 when the knob 14 is released from the finger, and the lower surface of the push-out portion 52 is not projected into the path of the clip 100 formed by the lower and upper casings 12 and 13, and therefore the clip 100 can be freely slid into the groove 24.

Figure 11:
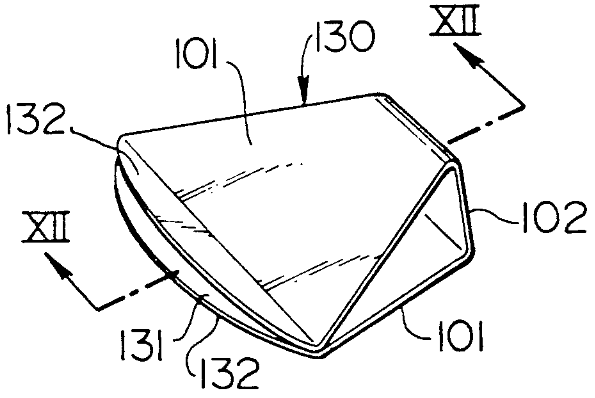
FIG. 11 is a perspective view showing another embodiment of the spring clip according to the present invention.
Figure 12:
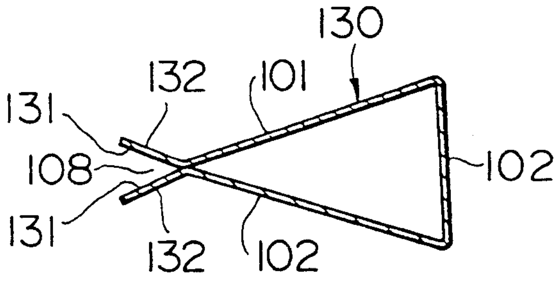
FIG. 12 is a vertical section view of the spring clip of FIG. 11 along XII—XII line.

In the embodiments described above, the clip 100 is made of synthetic resin, the thickness of the clip 100 is increased to make the clip 100 strong, and the slanting end surfaces 107 are formed at the front edges 103 by using the thickness of the clip 100 to thereby form the gap 108 which enters into the base portions 110 of the clip opening spring members 21. On the other hand, in the case where the clip is made of a metal plate having strength larger than that of a synthetic resin plate, and if the metal plate is thick, the elasticity of the spring leg portions 111 of the respective clip opening spring members 21 necessary for opening the grasping portions is required to be large. Further, the grasping force of the clip 100 becomes so large as to cause a probability that when the clip is removed from the bound documents, not only it is difficult to remove the clip but the documents at the upper and lower surface sides may be damaged. FIG. 11 illustrates therefore a second embodiment of the clip which is made of an elastic thin metal plate. In this embodiment, slanting end surfaces 131 for forming a gap 103 of a clip 130 are formed by bending front edges 132 of grasping portions 101 in the direction so as to separate from each other. The front edges 132 are made round so as not to form sharp corner portions respectively.

Figure 13:
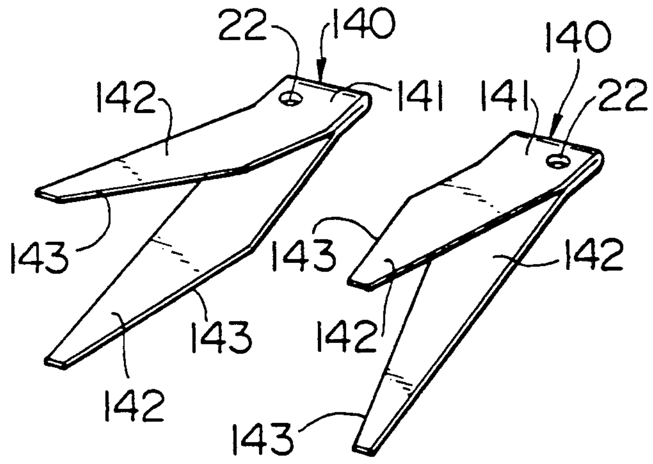
FIG. 13 is a perspective view showing another embodiment of the clip-opening portion.

Further, in the above embodiment, each of the clip opening spring members 21 is formed in a manner so that each of a pair of portions of a material extending in the same direction from another portion corresponding to the base portion 110 is reduced in thickness to about a half of the latter portion to thereby form a pair of spring leg portions 111. However, each of the clip opening spring members 21 may be formed by bending an elastic thin metal plate as shown in FIG. 13. That is, an elastic strip-like thin metal plate is folded at its substantially central portion and the folded portions are put on each other so as to form a base portion 141 having a predetermined length to thereby form a clip opening spring member 140. The portions extending from the front end of the base portion 141 are biased so as to separate from each other at the respective front ends thereof to thereby form two spring leg portions 142. The inner side edge of each of the leg portions 142 is cut so that the width of the front end of the leg portion 142 is narrower than the width of the base portion 141 at its end portion, thereby forming a slanting side edge 143 similar to the above-mentioned slanting side edge 112.

Referring to the preferred embodiments, the present invention has been described above. However, the description has been made by way of example for promoting the understanding of the invention, and the embodiments can be variously modified as far as the modification is not departed from the scope of the following claims.

What is claimed is:

1. A combination of a spring clip and a clip driver for binding materials by using the spring clip, said spring clip being made of a single elastic plate member and including a connection portion provided substantially at a longitudinal center of the elastic plate member and a pair of grasping portions each having one end integrally connected to the connection portion and a free end at an opposite side thereof, said free ends elastically contacting with each other and being opened against elasticity of the grasping portions when a force is applied to the free ends of the grasping portions so that the materials can be inserted between the free ends and elastically grasped therebetween when said force is removed, each of said grasping portions being defined by a front edge forming said free end, a rear edge forming a boundary between the grasping portion and the connection portion, and widthwise opposite side edges each extending between the front edge and the rear edge at widthwise opposite sides of the grasping portion, each of the grasping portion having a width wider at the front edge than at the rear edge, each of the widthwise opposite side edges extending substantially linearly, said grasping portions having end surfaces at the free ends respectively, said end surfaces being formed to have a gap therebetween at the front edges of the grasping portions, said clip driver including:

a lower casing having at its front end a lower opening portion forming a part of an insertion inlet for said materials, said lower casing having an upper surface on which at least one said clip is mounted with said grasping portions directed toward said insertion inlet so that said clip is slidable in a longitudinal direction of said clip driver;

an upper casing having at its front end an upper opening portion forming said insertion inlet together with said lower opening portion of said lower casing and having at its rear end a clip insertion inlet for inserting said clip and a rectangular opening at its front end side to extend in the longitudinal direction thereof;

a knob mounted in the rectangular opening in said upper casing, said knob being slidable in said longitudinal direction and being movable up and down within a predetermined range, said knob having a knob projection portion projected upward from said opening, a push-out portion formed on a front end of said knob projection portion so that said push-out portion comes to abut on said connection portion of said clip when said knob is lowered, and a projection portion rearward extending from a rear end of said knob projection portion;

a pair of clip opening spring members provided in said insertion inlet formed by said lower and upper casings for opening said grasping portions of said clip in opposite directions to each other, each of said clip opening spring members having a base portion having a thickness less than a distance of said gap of said clip, and a pair of spring leg portions extending from a front end of said base portion and elastically biased in the direction so as to separate from each other, said clip opening spring members being disposed in said casing so that the distance between opposite inner side edges of said two base portions is made longer than the width of said grasping portions at said rear edge of said clip while shorter than the width of said grasping portions at said front edge thereof, said pair of spring leg portions being tapered at front end side edges opposite to each other so that an interval between said front end opposite sides edges of said spring leg portions becomes wider than the width of said front edges of said clip as a distance from the base portion of the spring leg portion increases.

2. A combination according to claim 1, in which each of said clip opening spring members is made of an elastic metal plate in a manner so that portions extending in the same direction from a base portion are reduced in thickness to about a half to form two thin portions which are bent in the directions opposite to each other to thereby form said spring leg portions.

3. A combination according to claim 1, in which said clip opening spring member is made of an elastic thin metal plate in a manner so that said thin metal plate is folded so as to form said base portion at the folded portion, and portions extending from front ends of said base portion are biased so that front ends of said extending portions separate from each other to thereby make said extending portions said spring leg portions.

4. A combination according to claim 1, in which a substantially horizontally-projected projection portion is formed on a rear end surface of said lower casing and an engagement portion to be engaged with said knob projection portion is formed on a rear end portion of said upper casing so that said lower and upper casings are assembled in the condition that said engagement portion engages with said knob projection portion, the assembly of said lower and upper casings being fixed by means of a fastening band at an outer periphery thereof on said insertion inlet side.

5. A combination according to claim 1, in which substantially horizontally sideward projected and longitudinally extending rim portions are provided on opposite side surfaces of said opening of said upper casing, and in which said push-out portion of said knob has first lower projections formed on a lower surface thereof so as to engage with lower surfaces of said rim portions respectively when said knob is moved up, said knob projection portion of said knob has second lower projections formed on a lower surface thereof so as to engage with said lower surfaces of said rim portions respectively, and said knob projection portion of said knob has upper projections formed on opposite sides thereof for limiting downward movement of said knob, so that said knob is supported by said first lower projections, said second lower projections, and said upper projections so as to be slidable without coming off.

6. A combination according to claim 1, in which a limitation portion is formed on a lower surface at a rear end of said knob upper casing so as to abut on said projection portion of said knob to thereby limit retreating of said knob, and in which a rear end of said knob projection portion is tapered so as to point-contact with said limitation portion, said point-contact portion being positioned lower than an attachment portion of an elastic member.

7. A combination according to claim 1, in which an engagement portion to be engaged with said connection portion of said clip is formed on a front end of said push-out portion of said knob.

8. A combination according to claim 1, in which a cover portion is formed so as to rearward extend from a front end of said clip insertion inlet of said upper casing, said cover portion being formed so as to have elasticity so that said cover portion is able to be biased vertically, said cover portion being positioned so that a gap slightly narrower than a thickness of said connection portion of said clip is formed between a free end of said cover portion and a rear end of said clip insertion inlet.

* * * * *